(12) United States Patent
Argentine

(10) Patent No.: US 8,137,321 B2
(45) Date of Patent: Mar. 20, 2012

(54) INTRODUCER SHEATH

(75) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 11 days.

(21) Appl. No.: 12/778,240

(22) Filed: May 12, 2010

(65) Prior Publication Data

US 2011/0282286 A1   Nov. 17, 2011

(51) Int. Cl.
*A61M 5/178* (2006.01)
(52) U.S. Cl. .................................. 604/167.06
(58) Field of Classification Search .............. 604/167.06
See application file for complete search history.

(56) References Cited

U.S. PATENT DOCUMENTS

| | | | | |
|---|---|---|---|---|
| 4,673,393 A * | 6/1987 | Suzuki et al. | ............ | 604/167.04 |
| 4,846,836 A * | 7/1989 | Reich | ......................... | 623/23.68 |
| 4,960,412 A | 10/1990 | Fink | | |
| 5,000,745 A * | 3/1991 | Guest et al. | .................... | 604/256 |
| 5,057,084 A * | 10/1991 | Ensminger et al. | ....... | 604/167.04 |
| 5,092,846 A * | 3/1992 | Nishijima et al. | ....... | 604/167.04 |
| 5,180,365 A * | 1/1993 | Ensminger et al. | ....... | 604/288.03 |
| 5,364,372 A * | 11/1994 | Danks et al. | .................. | 604/264 |
| 5,376,077 A * | 12/1994 | Gomringer | .............. | 604/167.06 |
| 5,409,463 A * | 4/1995 | Thomas et al. | ........... | 604/167.04 |
| 5,643,227 A * | 7/1997 | Stevens | ......................... | 604/264 |
| 6,024,729 A * | 2/2000 | Dehdashtian et al. | ........ | 604/256 |
| 6,083,203 A * | 7/2000 | Yoon | ......................... | 604/167.01 |
| 6,352,520 B1 | 3/2002 | Miyazaki | | |
| 6,482,181 B1 | 11/2002 | Racenet et al. | | |
| 6,551,283 B1 * | 4/2003 | Guo et al. | ................ | 604/167.06 |
| 6,610,031 B1 * | 8/2003 | Chin | ......................... | 604/167.04 |
| 6,632,200 B2 * | 10/2003 | Guo et al. | ...................... | 604/247 |
| 7,081,106 B1 * | 7/2006 | Guo et al. | ................ | 604/167.06 |
| 7,172,580 B2 * | 2/2007 | Hruska et al. | ................. | 604/248 |
| 7,901,379 B2 * | 3/2011 | Argentine et al. | ........ | 604/167.06 |
| 2008/0157017 A1 * | 7/2008 | Macatangay et al. | ......... | 251/314 |
| 2009/0234290 A1 | 9/2009 | Fisher et al. | | |

FOREIGN PATENT DOCUMENTS

WO   WO 99/45996   9/1999

* cited by examiner

*Primary Examiner* — Jackie Ho
*Assistant Examiner* — Diva Ranade

(57) ABSTRACT

An introducer sheath includes a elongated sheath configured to be inserted into a blood vessel. The elongated sheath includes a central lumen configured to allow a surgical implement or medical device to pass therethrough. The introducer sheath also includes a hemostatic valve operatively connected to the sheath. The hemostatic valve is configured to prevent blood in the blood vessel from exiting the introducer sheath assembly when the elongated sheath is located in the blood vessel. The hemostatic valve includes a plurality of seals supported by a housing, including a front seal configured to provide a hemostatic seal with a guide wire, and a rear seal configured to provide a hemostatic seal with a range of sizes of implements and devices. The housing is configured to provide strain recovery for strain induced by displacement forces generated during movement of the implement or medical device through the plurality of seals.

20 Claims, 10 Drawing Sheets

INTRODUCER SHEATH

BACKGROUND

1. Field of the Invention

The present invention is directed to an introducer sheath having a hemostatic valve that can maintain hemostasis around surgical implements and medical devices having a wide variety of cross-sectional diameters during surgical procedures.

2. Background of the Invention

Introducer sheaths are used to assist in the introduction of guide wires, surgical implements, and medical devices into a patient's vascular system (typically an artery) for many different types of intravascular procedures. The introducer sheath and its associated dilator are designed to penetrate the skin and wall of the blood vessel and be positioned within the blood vessel so that surgical implements and medical devices may be advanced and withdrawn through the introducer sheath. In this way, even when multiple surgical implements and/or medical devices are used in a single procedure, there is a single placement of the introducer sheath through the skin and vessel wall.

Introducer sheaths typically include valves that generally fall into two basic categories: passive and active. A passive valve generally relies on the deformation of a resilient sealing body by the implement or medical device inserted through the valve to form the desired fluid tight seal. An active valve includes a mechanism that moves a sealing body into contact with the traversing implement or medical device.

A wide variety of passive and active valve structures for introducer sheaths have been proposed. While these structures have met with varying degrees of success and acceptance, they generally have suffered from a common disadvantage: sealing bodies (whether passive or active) that provide an effective hemostatic seal with a guide wire and with a wide range of cross-sectional diameters of surgical implements and medical devices. Passive valve structures tend to impose substantial frictional forces on at least some sizes of traversing implements, e.g., the larger sizes, thereby making is difficult for the user to insert and withdraw such implements into and out of the introducer sheath.

Despite the wide variety of introducer sheaths that have been proposed, the use of simple fixed o-rings or grommets for the valve remains common. While these simple sealing devices accommodate only a very narrow range of surgical implement diameters, the seals provided within that range tend to impose frictional forces that are low. In many cases, hemostasis cannot be achieved due to inadequate sealing, and many introducer sheaths leak when only a guide wire is placed in the introducer sheath.

Endovascular surgical procedures, such as the endovascular placement of vascular stents, grafts, stent-grafts, and other endoluminal prostheses for the treatment of abdominal aortic aneurysms and other vascular diseases, have been developed that place even more stringent demands on the introducer sheath. Such endovascular prosthetic placement procedures generally involve the use of relatively large prosthetic deployment catheters, typically having a French gauge in the range from about 11 Fr to about 26 Fr.

SUMMARY OF THE INVENTION

For these reasons, it is desirable to provide an introducer sheath with a valve that can provide a hemostatic seal with a guide wire, as well as with surgical implements and medical devices having a wide range of diameters, so that a single introducer sheath may be used with a guide wire and with varying diameters of implements and medical devices, yet impose a level of frictional forces on the traversing implements and medical devices that are acceptable to the user.

According to an aspect of embodiments of the invention, there is provided an introducer sheath that includes an elongated sheath configured to be inserted into a blood vessel. The elongated sheath includes a central lumen configured to allow a surgical implement or medical device to pass therethrough. The introducer sheath includes a hemostatic valve operatively connected to the sheath. The hemostatic valve is configured to prevent blood in the blood vessel from exiting the introducer sheath assembly when the elongated sheath is located in the blood vessel. The hemostatic valve includes a housing configured to sealingly support the sheath, and a front seal disposed within and supported by the housing. The front seal includes a cylindrical sidewall and a web extending transverse to the sidewall to define a cavity within the front seal. The web includes a central opening configured to provide a hemostatic seal with a guide wire when a portion of the guide wire is passed through the hemostatic valve, a first slit centered on the opening, and a plurality of elongated ribs equally spaced around the opening and radially extending away from the opening. The slit and the elongated ribs are configured to allow the surgical implant or medical device to pass through the front seal. The hemostatic valve also includes a first intermediate seal having a second slit oriented in a first direction. The first intermediate seal is supported by the front seal in the cavity. The hemostatic valve also includes a second intermediate seal disposed in abutment with the first intermediate seal and supported by the front seal in the cavity. The second intermediate seal has a third slit oriented in a second direction that is about 90° relative to the first direction. The first and second intermediate seals are configured to support and center the guide wire in the opening of the front seal when the portion of the guide wire is passed though the hemostatic valve, to allow the surgical implement or medical device to pass through the first and second intermediate seals, and to create hemostasis when no guide wire, surgical implement, or medical device is present in the hemostatic valve. The hemostatic valve also includes a rear seal disposed in abutment with the front seal so that the first intermediate seal and the second intermediate seal are located in between the front seal and the rear seal. The rear seal has a web with an opening. The web is configured to provide a hemostatic seal with a plurality of different sizes of surgical implements and medical devices when each implement and device is individually passed through the hemostatic valve. The plurality of different sizes ranges between about 3 mm and about 9 mm in diameter. The housing is configured to provide strain recovery for strain induced by displacement of the seals caused by movement of the implement or device through the front seal, the first intermediate seal, the second intermediate seal, and the rear seal.

According to an aspect of the present invention, there is provided a hemostatic valve for an introducer sheath. The hemostatic valve includes a housing, and a front seal disposed within and supported by the housing. The front seal includes a cylindrical sidewall and a web extending transverse to the sidewall to define a cavity within the front seal. The web includes a central opening configured to provide a hemostatic seal with a guide wire when a portion of the guide wire is passed through the hemostatic valve, a first slit centered on the opening, and a plurality of elongated ribs equally spaced around the opening and radially extending away from the opening. The slit and the elongated ribs are configured to allow the surgical implant or medical device to pass through the front seal. The hemostatic valve also includes a first intermediate seal having a second slit oriented in a first direction. The first intermediate seal is supported by the front seal in the cavity. The hemostatic valve also includes a second intermediate seal disposed in abutment with the first intermediate seal and supported by the front seal in the cavity. The second intermediate seal has a third slit oriented in a second direction that is about 90° relative to the first direction. The first and second intermediate seals are configured to support and center the guide wire in the opening of the front seal when the portion of the guide wire is passed though the hemostatic valve, to allow the surgical implement or medical device to pass through the first and second intermediate seals, and to create hemostasis when no guide wire, surgical implement, or medical device is present in the hemostatic valve. A rear seal is disposed in abutment with the front seal so that the first intermediate seal and the second intermediate seal are located in between the front seal and the rear seal. The rear seal has a web with an opening. The web is configured to provide a hemostatic seal with a plurality of different sizes of surgical implements and medical devices when each implement and device is individually passed through the hemostatic valve. The plurality of different sizes range between about 3 mm and about 9 mm in diameter. The housing is configured to provide strain recovery for strain induced by displacement caused by movement of the implement or device through the front seal, the first intermediate seal, the second intermediate seal, and the rear seal.

BRIEF DESCRIPTION OF THE DRAWINGS

Embodiments of the invention will now be described, by way of example only, with reference to the accompanying schematic drawings in which corresponding reference symbols indicate corresponding parts. At least one drawing may be to scale.

DETAILED DESCRIPTION

The following detailed description is merely exemplary in nature and is not intended to limit the invention or the application and use of the invention. There is no intention to be bound by any expressed or implied theory presented in the preceding technical field, background, brief summary or the following detailed description.

Figure 1:
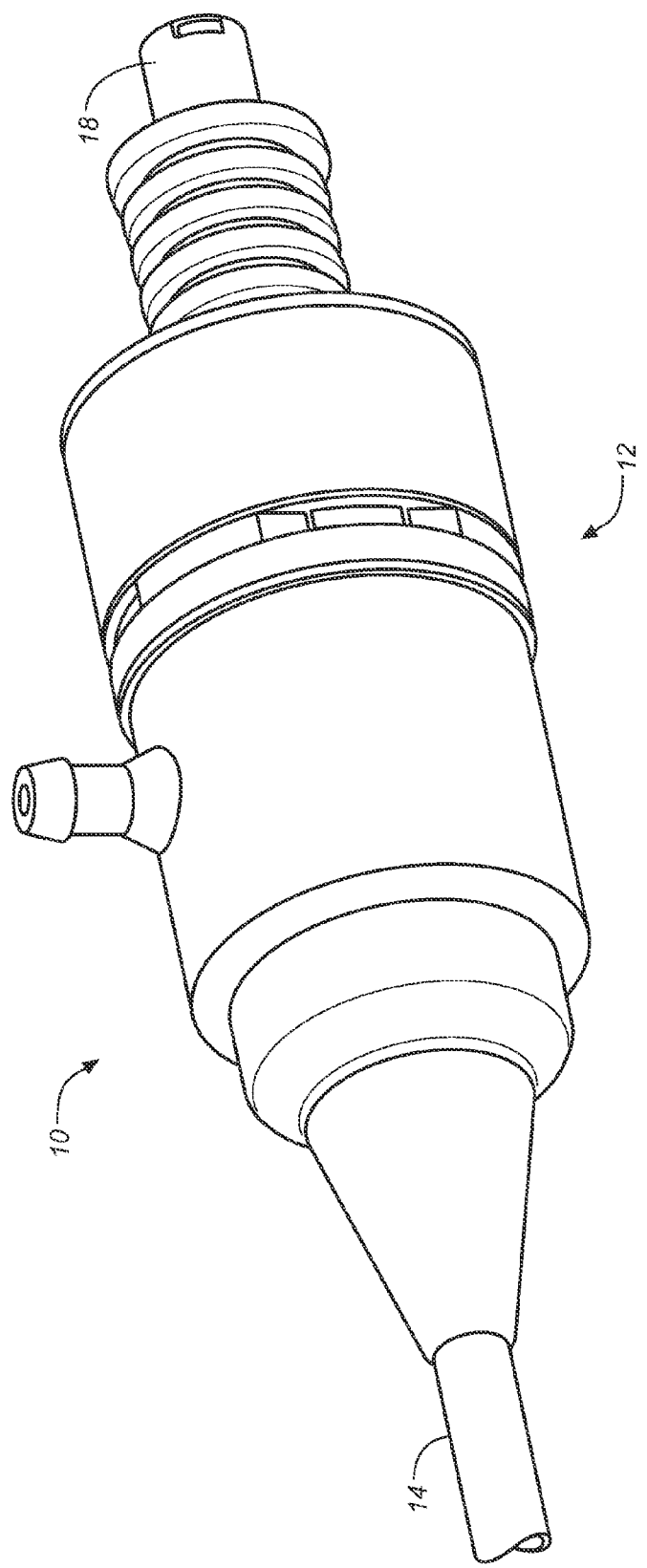
FIG. 1 is a oblique view of an introducer sheath according to an embodiment of the present invention.
Figure 2:
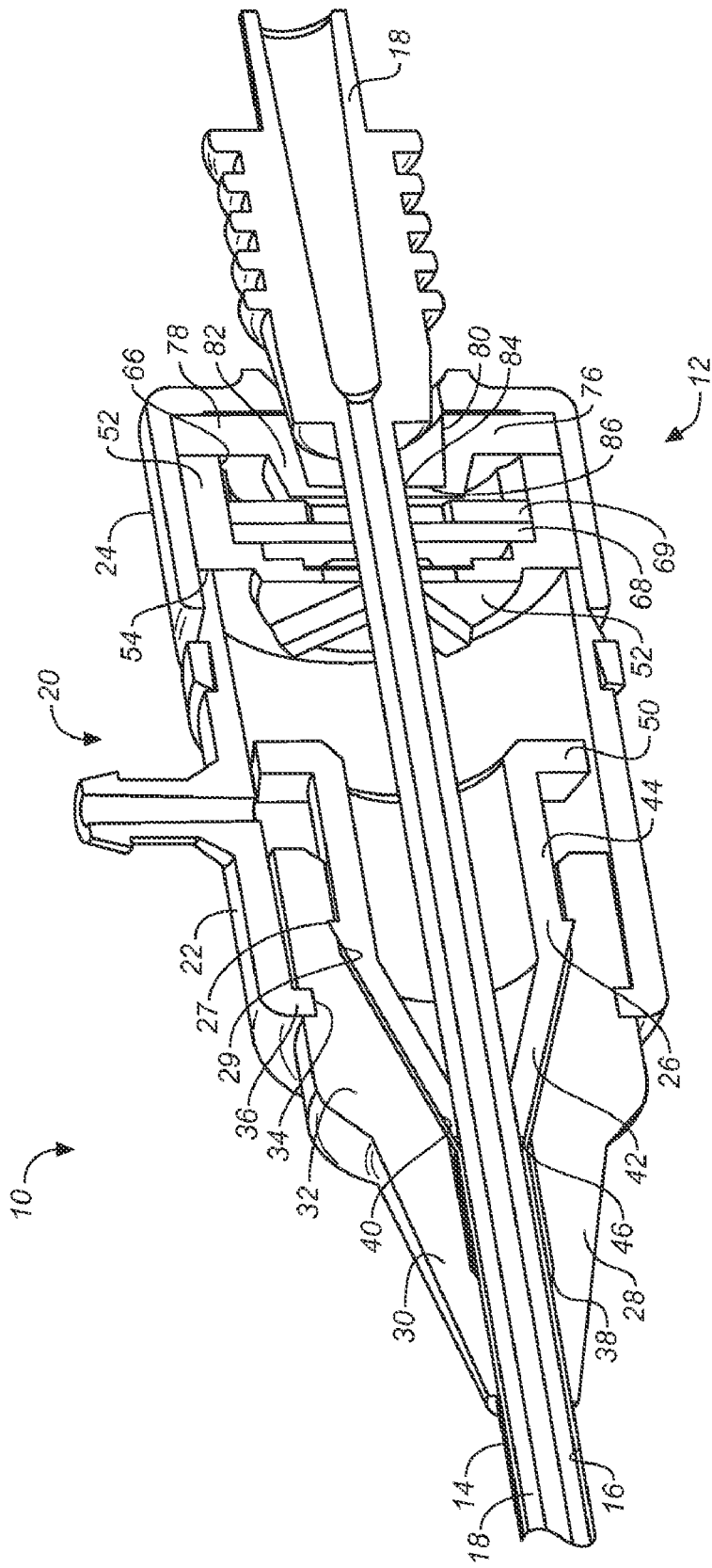
FIG. 2 is a cross-sectional oblique of the introducer sheath of FIG. 1.

FIGS. 1 and 2 schematically illustrate an introducer sheath 10 according to an embodiment of the invention. As illustrated, the introducer sheath 10 includes a hemostatic valve 12, and an elongated sheath 14 that extends from one end of the valve 12. The sheath 14 is a substantially cylindrical and elongated hollow member that is configured to be inserted into a body lumen through which blood flows, such as a blood vessel, as discussed in further detail below. An interior lumen 16 (see FIG. 2) of the sheath 14 is sized and configured to receive, for example, a dilator 18, although any suitably sized surgical implement or medical device that is to be introduced to the blood vessel may be introduced via the sheath 14 of the introducer sheath 10.

In an embodiment, the introducer sheath 10 may include multiple sheaths 14 having different diameters that are part of a kit so that the smallest diameter sheath possible may be used during the surgical procedure. For example, one sheath as part of the kit may be configured to handle 11-13 Fr catheters, another sheath may be configured to handle 14-16 Fr catheters, and so on.

As illustrated in FIGS. 1 and 2, one end of the sheath 14 is operatively connected to the valve 12. The valve 12 includes an outer housing 20, which includes a inner front portion 22 and a inner back portion 24 that is connected to the inner front portion 22, and an inner housing 26 that is operatively connected to the inner front portion 22 of the outer housing 20. The valve 12 also includes a sheath seal 28 that is connected to the inner front portion 22 of the outer housing 20 and is also configured to receive and support the inner housing 26, and the sheath 14, as illustrated in FIG. 2.

The sheath seal 28 includes a substantially conical portion 30 and a substantially cylindrical portion 32. The cylindrical portion 32 has a groove 34 on an outside surface that is configured to receive a lip or inner flange 36 of the inner front portion 22 of the outer housing 20, thereby allowing the cylindrical portion 32 to extend into the outer housing 20, while being secured to the outer housing 20. The conical portion 30 of the sheath seal 28 has an inner lumen 38 that is configured to sealingly receive the sheath 14 so that blood cannot flow in between the sheath seal 28 and the sheath 14. In an embodiment, the inner lumen 38 may have a diameter that is less than the outer diameter of the sheath 14 so that an interference fit may be achieved. As part of the kit having different sizes of sheaths, the kit may also include different sheath seals 28 that have inner lumens 38 that are each configured to sealingly receive one of the sheaths 14 so that a seal may be provided for every sheath 14.

The sheath seal 28 also includes a cavity 40 that extends from the inner lumen 38 and is configured to receive a conical portion 42 of the inner housing 26 and at least a portion of a cylindrical portion 44 of the inner housing 26. As illustrated in FIG. 2, the inner housing 26 is generally hollow and has an opening 46 at an apex of the conical portion 42 that is configured to support the dilator 18, or any other suitably sized surgical implement or medical device, that is inserted into the valve 12 and into the sheath 14. A flange 50 is located at an end of the inner housing 26 that is opposite the opening 46. The flange 50 may be configured to engage an inner surface of the outer housing 20, as illustrated in FIG. 2, so that the outer housing 20 supports the inner housing 26.

The inner housing 26 also includes an annular protrusion 27 having a cross-section of a barb-like structure that is configured to be received by an annular recess 29 in an interior surface of the sheath seal 28 having a corresponding shape for receiving and locking with the annular protrusion 27 of the inner housing 26. This locking relation between the annular protrusion 27 and the annular recess 29 assists in keeping the sheath seal 28 engaged with an interior of the inner front portion 22 of the outer housing 20, as well as assists in preventing the sheath 14 from being pushed into the outer housing 20 when the sheath 14 is being inserted into a blood vessel.

Figure 3:
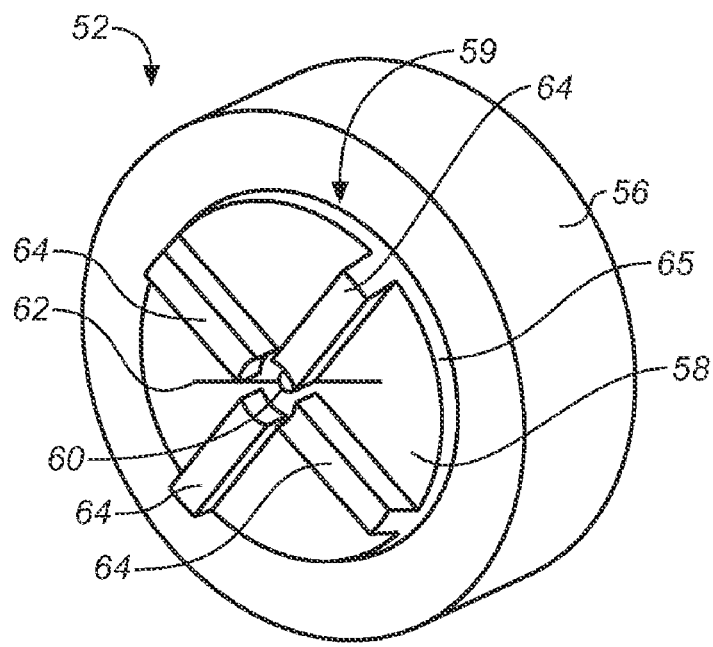
FIG. 3 is a oblique view of a front seal of the introducer sheath of FIGS. 1 and 2.

A front seal 52 is supported by the inner back portion 24 of the outer housing 20, and is configured to engage an end 54 of the inner front portion 22 of the outer housing 20 that is opposite the lip or inner flange 36. Further details of an embodiment of the front seal 52 are illustrated in FIG. 3. As illustrated, the front seal 52 includes a substantially cylindrical sidewall 56 and a web 58 that extends transversely across the sidewall 56 so as to form an outer face that has a central, substantially cylindrical raised portion 59. The web 58 includes a central opening 60, a slit 62 that is centered on and passes through the opening 60, and optionally a plurality of ribs 64 that extend from an outer edge 65 of the raised portion 59 towards the central opening 60. The central opening 60 is configured to form a hemostatic seal with a guide wire when the guide wire passes therethrough, but is not configured to support the guide wire. The slit 62 is configured to allow devices, such as surgical implements or medical devices, such as a catheter or the dilator 18 illustrated in the Figures, to pass through the front seal 52 with nominal resistance. The optional plurality of ribs 64 are configured to provide an inertial structure configure to assist in closing the slit 62 when the device is removed from the valve 12. Although four ribs 64 are illustrated in FIG. 3, more or less ribs may be used, and as can be seen in later figures the ribs on this side of the front seal are absent completely. The illustrated embodiment is not intended to be limiting in any way.

Figure 4:
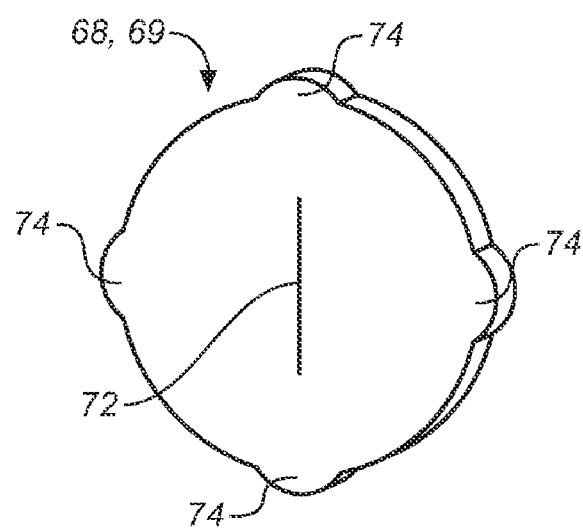
FIG. 4 is a oblique view of an intermediate seal of the introducer sheath of FIGS. 1 and 2.

As illustrated in FIG. 2, the front seal 52 includes a cavity 66 that is configured to support two intermediate seals 68, 69. The two intermediate seals 68, 69 may have substantially the same disc-like structure 70, an embodiment of which is illustrated in FIG. 4. As illustrated, the disc-like structure 70 of each seal 68, 69 includes a slit 72 that extends across the center of the of the disc-like structure 70, and a plurality of circumferential protrusions 74 that radially extend away from the center of the disc-like structure 70. The slit 72 when relaxed in its closed position configuration is fluid tight to blood at expected ranges of normal human blood pressure, e.g., 140/80 mm-Hg. Each of the protrusions 74 is configured to be received by a matching recess in the cavity 66 of the front seal 52. Upon assembly, the intermediate seals 68, 69 are oriented within the front seal 52 so that the slits 72 are oriented 90° apart. The intermediate seals 68, 69 are configured to support a guide wire when the guide wire is passed through the valve 12 and to center the guide wire in the outer housing 20 and in relationship with the opening 60 of the front seal 52.

As illustrated in FIG. 2, a rear seal 76 includes a flange 78 that is configured to engage the front seal 52 on one side, and to engage the inner back portion 24 of the outer housing 20 on the opposite side so that when the inner back portion 24 of the housing 20 is connected to the inner front portion 22 of the housing 20, the rear seal 76 seals with the front seal 52, with the intermediate seals 68, 69 being located therebetween. The flange 78 includes an opening 80 that is configured to receive the device being inserted into the introducer sheath 10, such as the dilator 18. As illustrated, the rear seal 76 also includes a central raised portion 82 that is configured to press against the intermediate seal 69. The raised portion 82 may have an opening 84 that is smaller than the opening 80 in the flange 78, but is configured to allow the dilator 18 to pass through the rear seal 76. In an embodiment, the opening 84 may be surrounded by a thin web 86 that is configured to stretch when the larger diameter dilator 18 passes through the opening such that the skirt 86 allows the dilator 18 to be moved relative to the rear seal 76 with some resistance and provide a hemostatic seal with the dilator 18.

Figure 5:
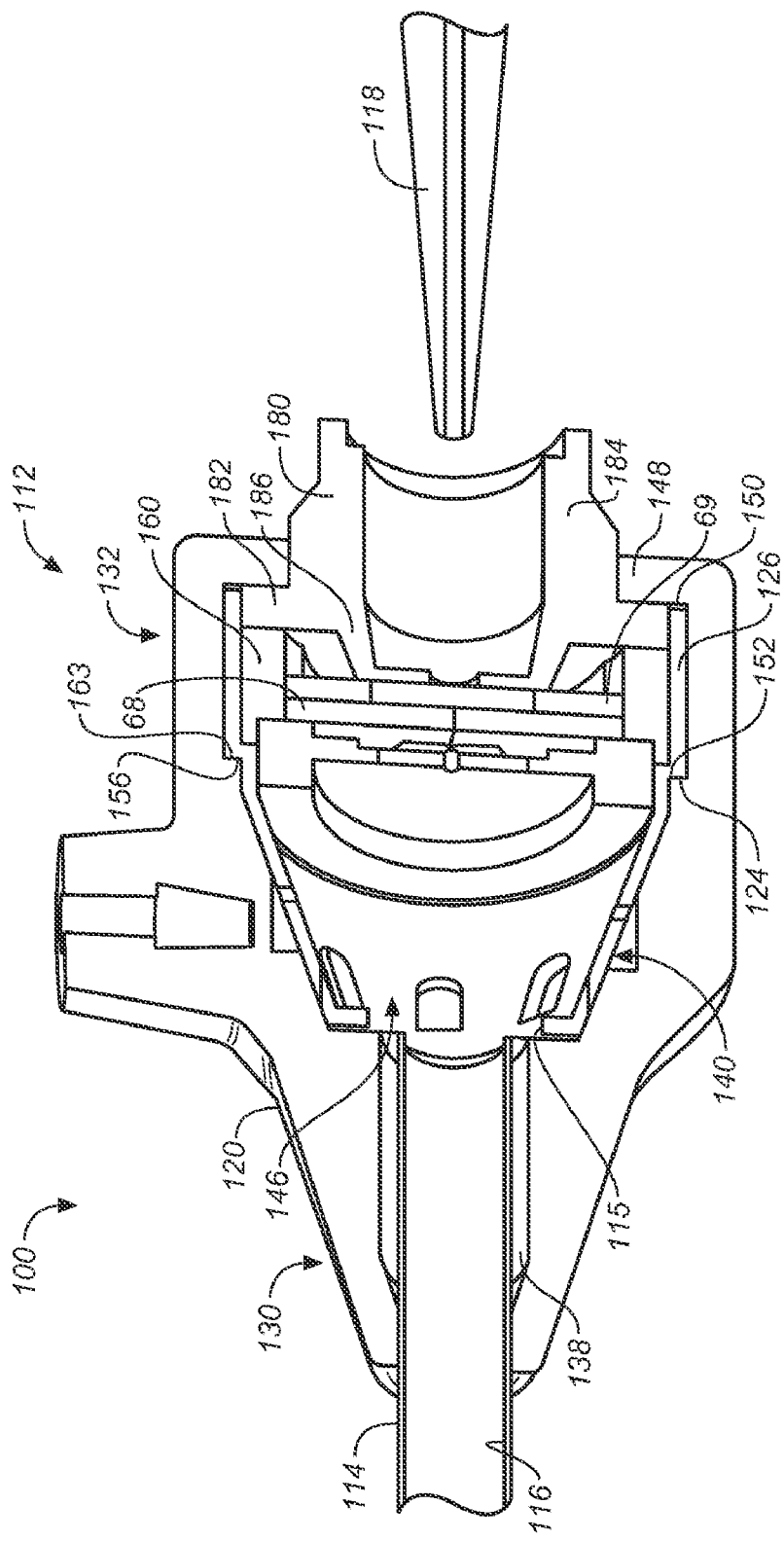
FIG. 5 is a cross-sectional oblique view of an introducer sheath according to an embodiment of the present invention.
Figure 6:
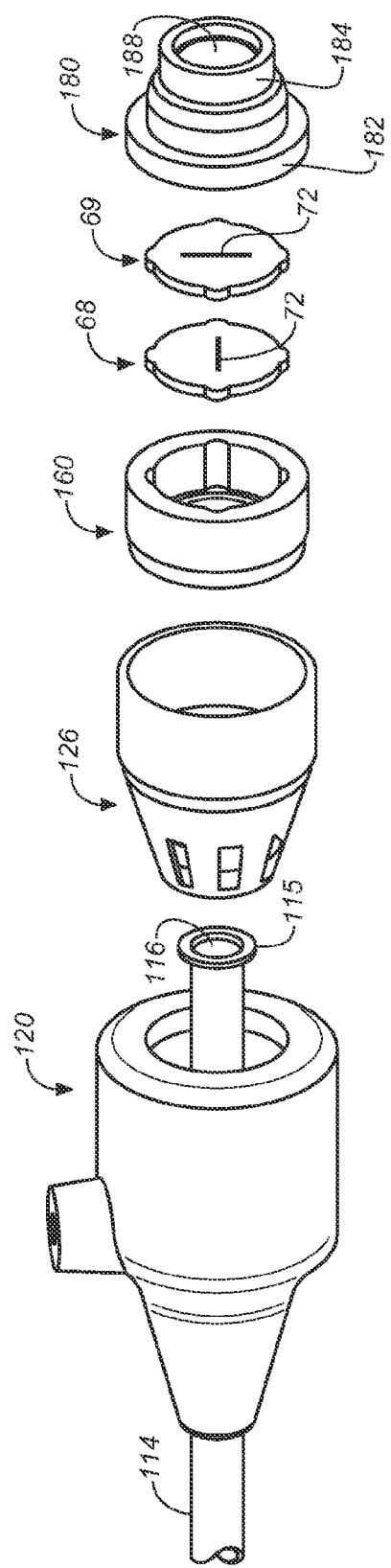
FIG. 6 is an exploded oblique view of the introducer sheath of FIG. 5.

FIGS. 5 and 6 illustrate an introducer sheath 100 according to an embodiment of the present invention. As illustrated, the introducer sheath 100 includes a hemostatic valve 112, and an elongated sheath 114 that extends from one end of the valve 112. In an embodiment, the sheath 114 may be of the same design as the sheath 14 discussed above. As illustrated, the sheath 114 may include a flange 115 at one end of the sheath 114 that is located within the valve 112. An interior lumen 116 of the sheath 114 is sized and configured to receive, for example, a dilator 118, although any suitably sized surgical implement or medical device that is to be introduced to the blood vessel may be introduced via the sheath 114 of the introducer sheath 100.

As illustrated in FIGS. 5 and 6, one end of the sheath 114 is operatively connected to the valve 112. The valve 112 includes an outer housing 120, and an inner housing 126 that is supported by the outer housing 120, as discussed in greater detail below. As illustrated, the flange 115 of the sheath 114 may be located between a portion of the inner housing 126 and the outer housing 120.

The outer housing 120 includes a substantially conical portion 130 and a substantially cylindrical portion 132. The conical portion 130 of the outer housing 120 has an inner lumen 138 that is configured to sealingly receive the sheath 114 so that blood cannot flow in between the outer housing 120 and the sheath 114. In an embodiment, the inner lumen 138 may have a diameter that is less than the outer diameter of the sheath 114 so that an interference fit may be achieved. As compared to the embodiment of the valve 12 illustrated in FIGS. 1 and 2, the outer housing 120 of the valve 112 illustrated in FIGS. 5 and 6 provides the function of both the outer housing 20 and the sheath seal 28.

Figure 7:
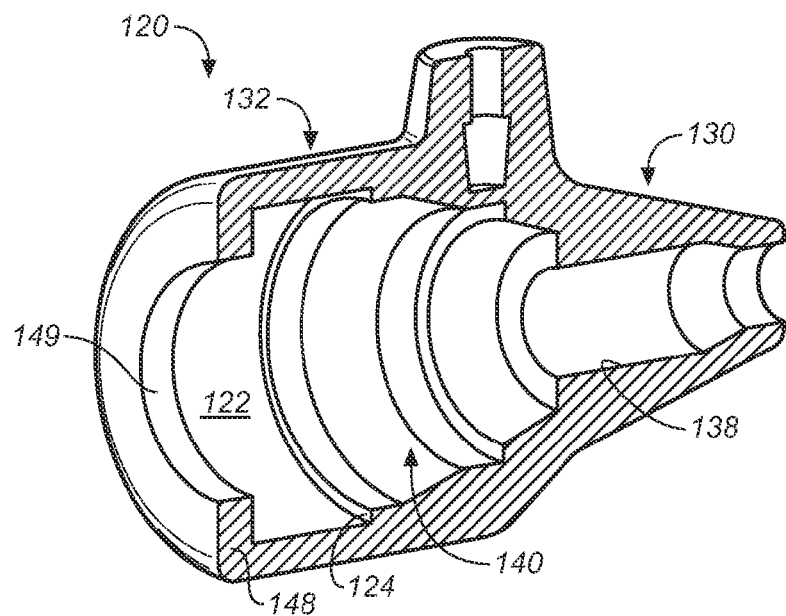
FIG. 7 is a cross-sectional oblique view of an outer housing of the introducer sheath of FIGS. 5 and 6.
Figure 8:
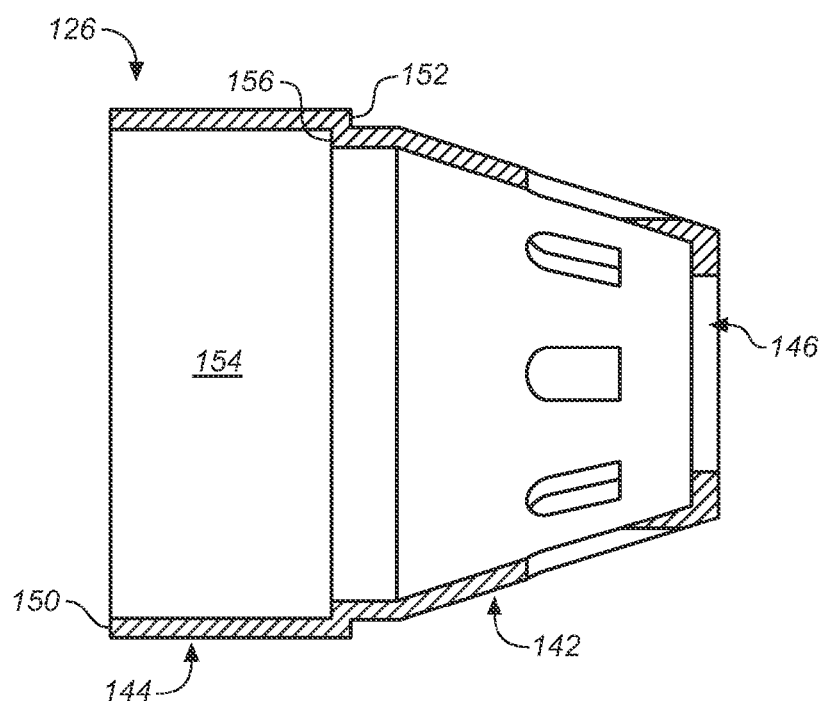
FIG. 8 is a cross-sectional view of an inner housing of the introducer sheath of FIGS. 5 and 6.

FIG. 7 and FIG. 8 illustrate the outer housing 120 and the inner housing 126 turned in the opposite direction in greater detail. The outer housing 120 also includes a cavity 140 that extends from the inner lumen 138 and is configured to receive a conical portion 142 of the inner housing 126 and a cylindrical portion 144 of the inner housing 126. The inner housing 126 is generally hollow and has an opening 146 at an end of the conical portion 142 that is configured to support the dilator 118, or any other suitably sized surgical implement or medical device, that is inserted into the valve 112 and into the sheath 114.

As shown in FIG. 7, in addition to the inner lumen 138 and the cavity 140, the outer housing 120 includes a lip or inner flange 148 and a opening 149 in the inner flange 148 that has a diameter that is less that the greatest diameter of the cavity 140. The inner flange 148 is configured to abut an end 150 of the inner housing 126, as shown in FIG. 5. An interior surface 122 of the outer housing 120 that defines the cavity 140 includes an inner circumferential ledge 124 that is configured to abut an outer circumferential ledge 152 of the inner housing 126, as also shown in FIG. 5.

As illustrated in FIG. 8, an interior surface 154 of the inner housing 126 also includes an inner circumferential ledge 156 where a transition between the cylindrical portion 144 and the conical portion 142 of the inner housing 126 is located. The inner circumferential ledge 156 and the outer circumferential ledge 152 of the inner housing 126 are slightly axially offset from one another.

Figure 9:
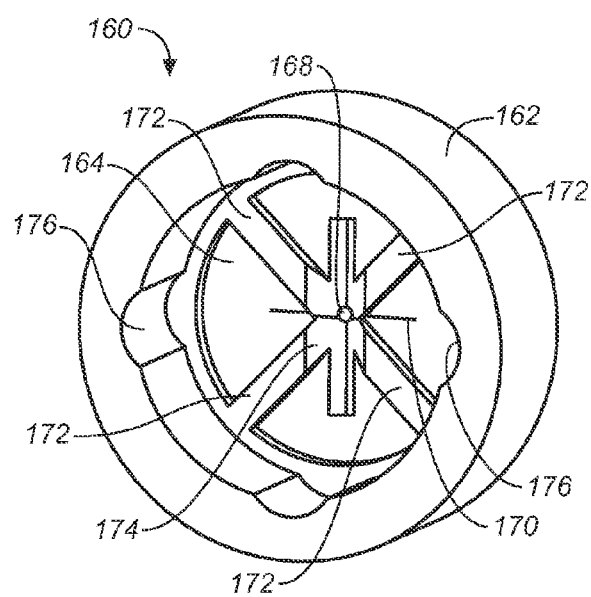
FIG. 9 is a oblique view of a front seal of the introducer sheath of FIGS. 5 and 6.
Figure 10:
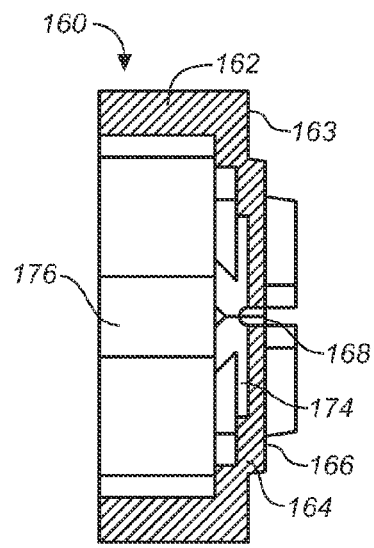
FIG. 10 is a cross-sectional view of the front seal of FIG. 9.

A front seal 160 is disposed within and is supported by the inner housing 126, as illustrated in FIG. 5. Further details of the front seal 160 are illustrated in FIGS. 9 and 10. As illustrated, the front seal 160 includes a substantially hollow cylindrical sidewall 162 and a web 164 that extends transversely (spans) across the space between the ring of the sidewall 162 so as to form an outer face 166. An outer surface of the sidewall 162 is stepped, so that a circumferential ledge 163 is formed, as illustrated in FIG. 10. The circumferential ledge 163 of the front seal 160 is configured to abut against the inner circumferential ledge 156 of the inner housing, as illustrated in FIGS. 5 and 8.

The web 164 includes a central opening 168, a slit 170 that is centered on and passes through the opening 168, a plurality of ribs 172 that extend radially inward from an interior surface of the sidewall 162 towards the opening 168, and a recess 174 that extends across the opening 168 at an angle of about 90° relative to the slit 170. As illustrated in FIG. 9, an end of each rib 172 near the opening 168 is tapered as the ribs transition into the recess 174. The central opening 168 is configured to form a hemostatic seal with a guide wire when the guide wire passes therethrough, but is not configured to support the guide wire (meaning the weight of the guide wire alone on the web 164 would distort the shape of the opening to prevent hemostasis). In an embodiment, the opening 168 may have a diameter of between about 0.87 mm and about 0.90 mm. In an embodiment, the opening 168 may have a diameter of about 0.89 mm.

The slit 170 is configured to allow devices, such as the dilator 118, to pass through the front seal 160 with nominal resistance. The recess 174 and the plurality of ribs 172 are configured to provide an inertial (support) structure to allow the slit 170 to open when the device is inserted into the valve 112, as well as to close (recover its strain) when the device is removed from the valve 12. Although four ribs 172 are illustrated in FIG. 9, more or less ribs may be used.

As illustrated in FIG. 9, an inner surface of the sidewall 162 of the front seal 160 includes a plurality of recesses 176. The recesses (half cylindrical slots) 176 are configured to receive the protrusions 74 of the intermediate seals 68, 69 that are shown in FIG. 4. As illustrated in FIG. 5, the intermediate seals 68, 69 are disposed within and supported by the front seal 160. The same intermediate seals 68, 69 discussed above with respect to FIG. 4 may be used in the embodiment of the introducer sheath 100 of FIGS. 5 and 6. As illustrated in FIG. 6, the intermediate seals 68, 69 are oriented relative to each other so that the slits 72 of the seals 68, 69 are oriented 90° apart. The intermediate seals 68, 69 are configured to support a guide wire (or other device) when the guide wire is passed through the valve 112 and to center the guide wire in the outer housing 120 and in relationship with the opening 168 in the front seal 160.

Figure 11:
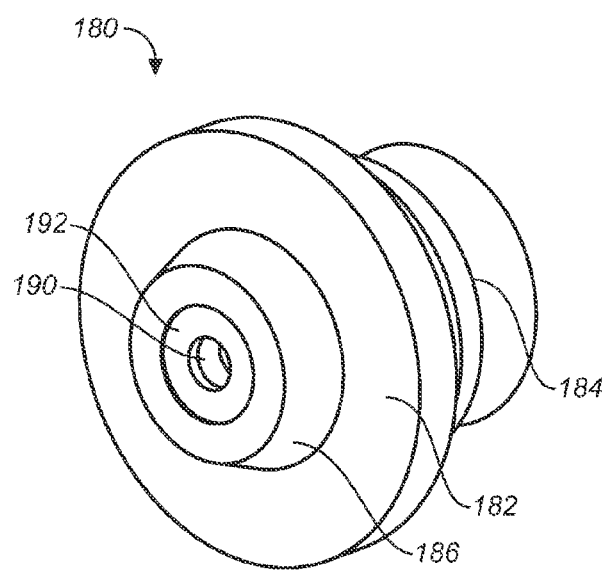
FIG. 11 is a oblique view of a rear seal of the introducer sheath of FIGS. 5 and 6.

As illustrated in FIGS. 5 and 6, the valve 112 also includes a rear seal 180. An embodiment of the rear seal 180 is illustrated in greater detail in FIG. 11. As illustrated, the rear seal 180 includes a flange 182, and a main body portion 184 that extends from one side of the flange 182 (as shown in FIG. 6). A smaller body portion 186 having a smaller diameter and axial length than the main body portion 184 extends from the opposite side of the flange 182 as the main body portion 184, as illustrated in FIG. 11. The main body portion 184 includes a large opening 188 (see FIG. 6) that has a diameter that is larger than the diameter of the implement or device that is to be inserted into the introducer sheath 100. The smaller body portion 186 includes a smaller opening 190 that is larger than the opening 168 in the front seal 160, but is smaller than the large opening 188 of the main body portion 184. The smaller opening 190 has a diameter that is larger than the diameter of the guide wire that is inserted into the introducer sheath 100, but smaller than the smallest diameter of the implement or device that is inserted into the introducer sheath 100 so that a hemostatic seal may be formed between the rear seal 180 and the device, such as the dilator 118. The opening 190 is formed in a thin flexible web 192 that is configured to stretch when the dilator 118 is pushed through the rear seal 180. As illustrated in FIG. 5, the smaller body portion 186 is configured to abut against the intermediate seal 69, and the flange 182 is configured to be disposed within the inner housing 126 and between an end of the front seal 160 and the inner flange 148 of the outer housing 120. Compressive forces may be applied on the flange 182 by the front seal 160 and the outer housing 120 to create a seal between the rear seal 180 and the outer housing 120 so that any blood that enters the conical portion 142 of the inner housing 126 cannot exit the outer housing 120 via the opening 149. A side port (not numbered) can function as an aspiration connection where a needle end of a syringe may be used to pierce the thin wall at the end of the port to perform aspiration functions using a syringe and a needle.

Figure 12:
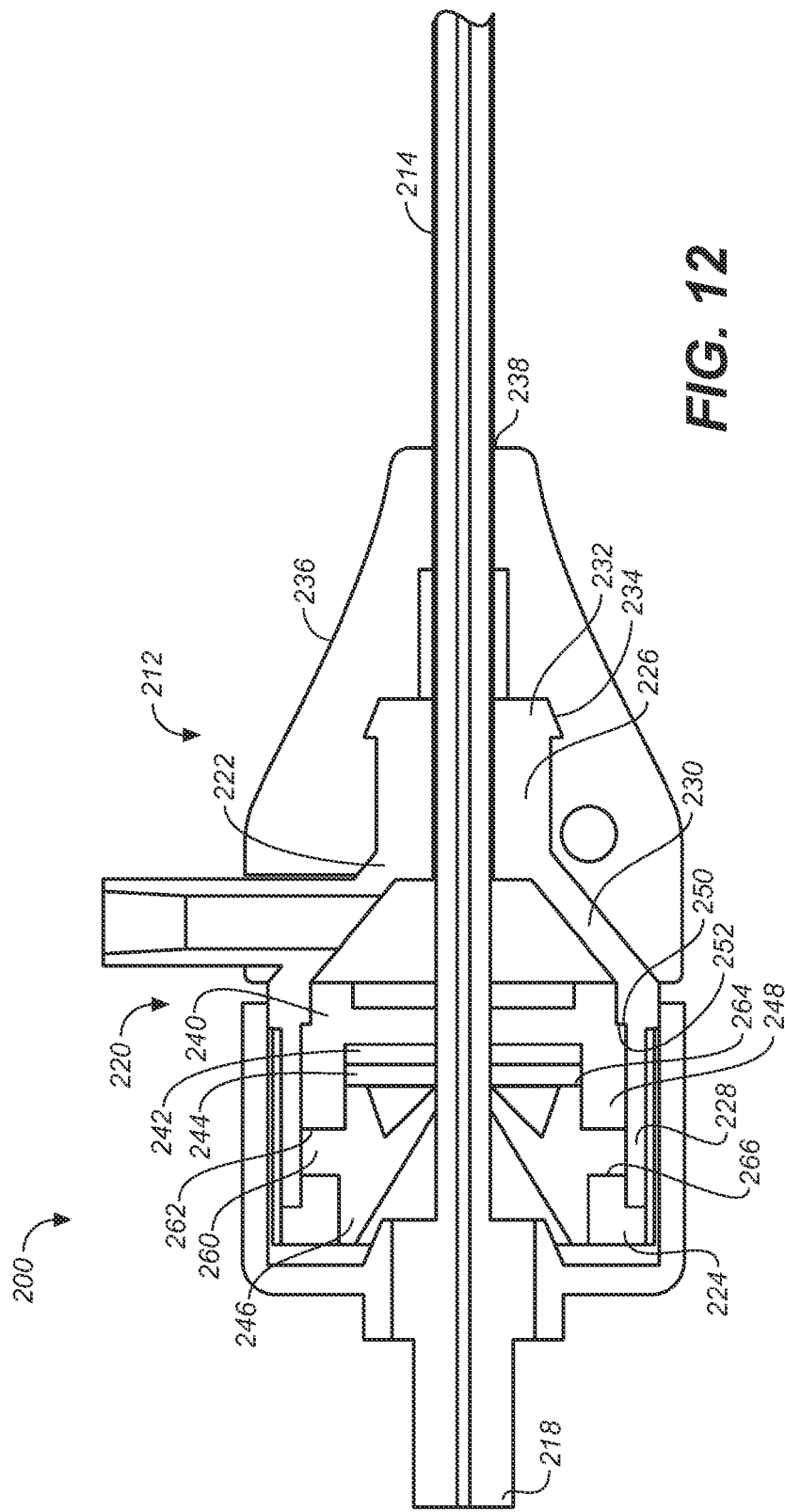
FIG. 12 is a cross-sectional view of an introducer sheath according to an embodiment of the present invention.
Figure 13:
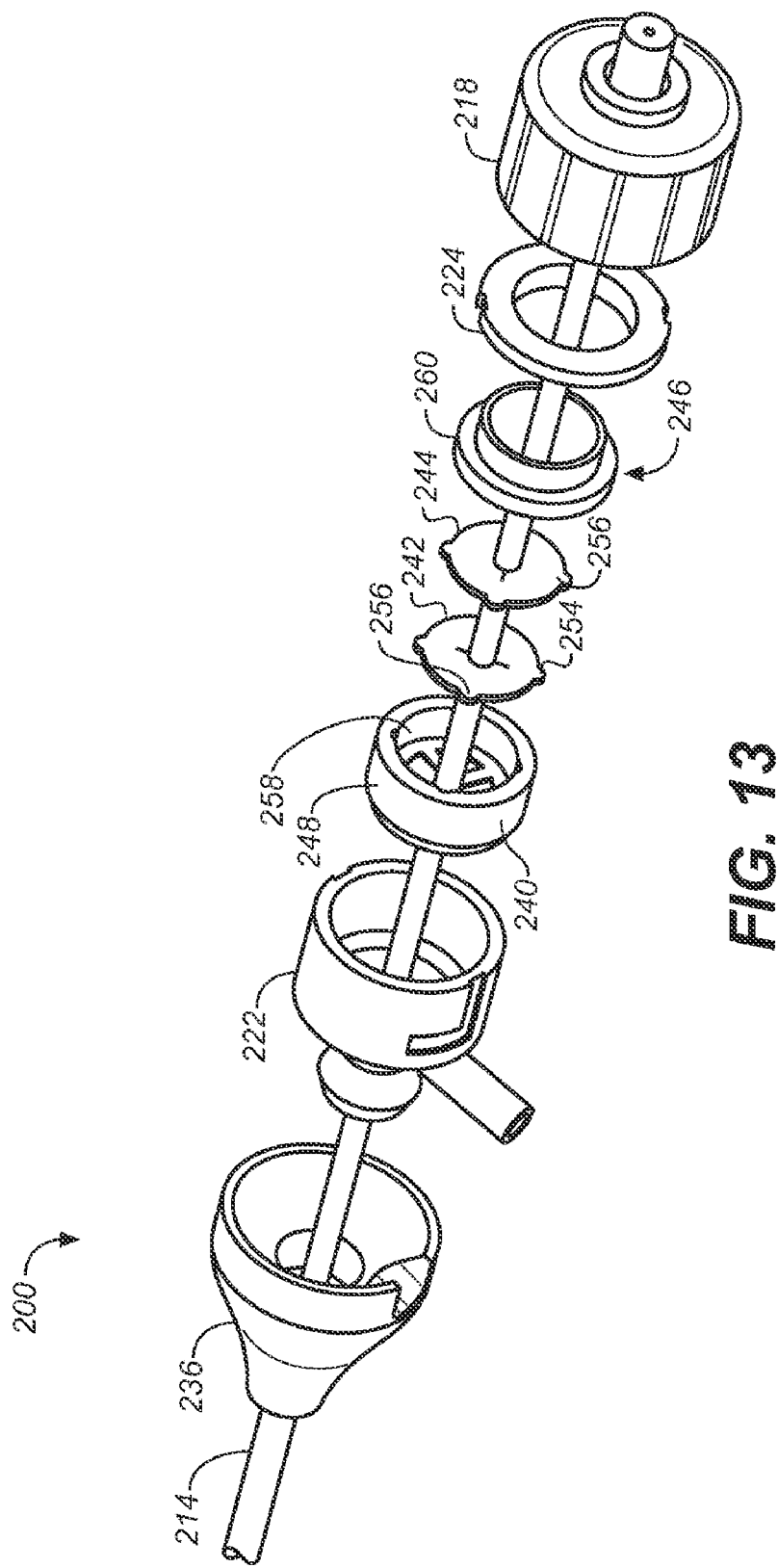
FIG. 13 is an exploded oblique view of the introducer sheath of FIG. 12.
Figure 14:
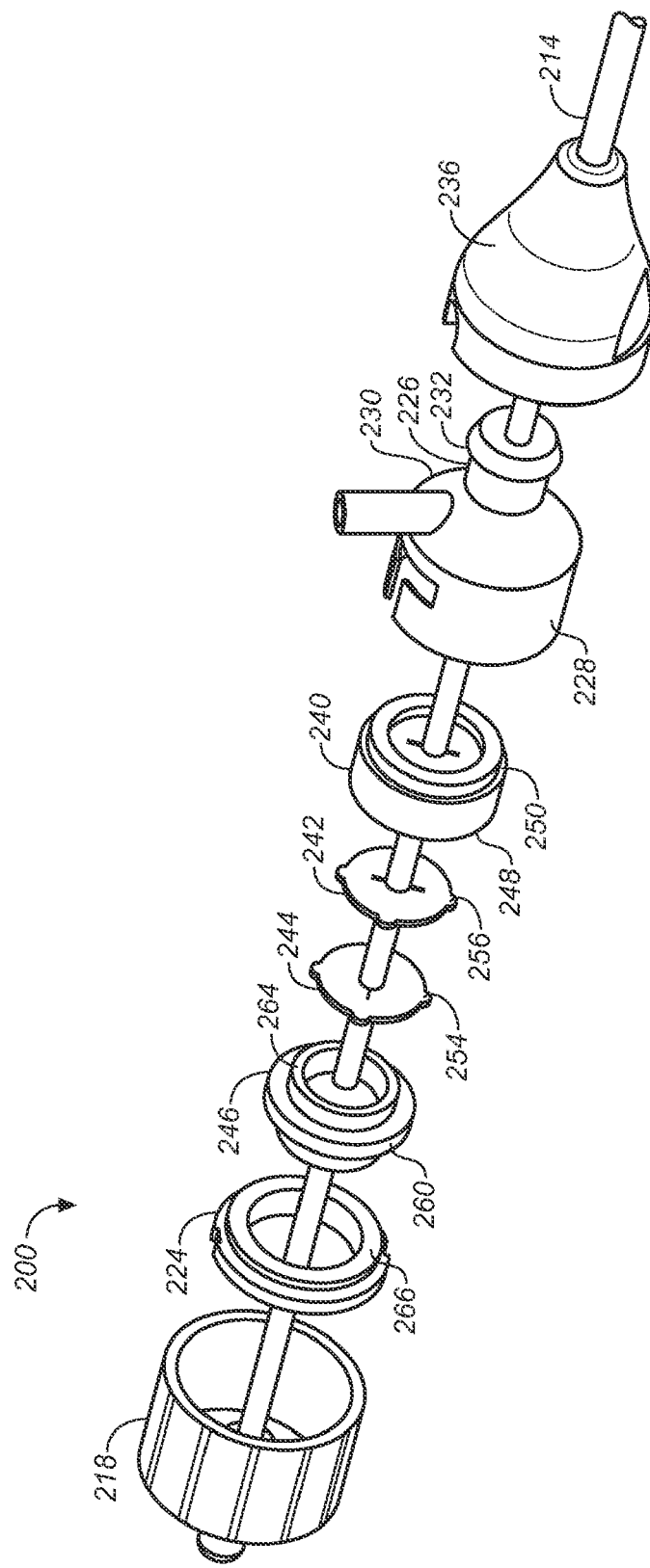
FIG. 14 is another exploded oblique view of the introducer sheath of FIGS. 12 and 13.

FIGS. 12-14 illustrate an introducer sheath 200 of another embodiment. As illustrated in FIG. 12, the introducer sheath 200 includes an elongated sheath 214 and a hemostatic valve 212 that supports the sheath 214. A dilator 218 is shown to be inserted into the introducer sheath 214, although any suitable surgical implement or medical device that needs to be introduced to a blood vessel via the introducer sheath 200 may by used in place of the dilator 218. Because many of the functions of the parts of the introducer sheath 200 illustrated in FIGS. 12-14 are the same as the functions provided by corresponding parts of the introducer sheaths 10, 100 described above, generally only differences in the structures of various parts will be discussed herein.

For example, the valve 212 includes a housing 220, including a inner front portion 222 and a inner back portion 224 that is operatively connected to the inner front portion 222. The inner front portion 222 generally includes a first cylindrical portion 226 having a first diameter, a second cylindrical portion 228 having a second diameter that is greater than the first diameter, and a conical portion 230 that connects the first cylindrical portion 226 and the second cylindrical portion 228. The first cylindrical portion 226 has tapered flange 232 at one end thereof that is configured to be received by an annular recess 234 of a sheath seal 236.

The sheath seal 236 is configured to be operatively connected to the inner front portion 222 of the housing 220 via the annular recess 234 and the flange 232, which have corresponding engagement surfaces. The sheath seal 236 includes a central lumen 238 that is configured to receive the sheath 214 in a manner that creates a seal with the sheath 214 so that blood cannot pass from inside the sheath seal 236 to outside the sheath 214 between the sheath seal 236 and the sheath 214.

The second cylindrical portion 228 of the housing is configured to receive a front seal 240, a first intermediate seal 242, a second intermediate seal 244, and at least a portion of a rear seal 246, as illustrated in FIG. 12. The front seal 240 may have the same or substantially the same design as the front seal 52 shown in greater detail in FIG. 3 or the front seal 160 shown in greater detail in FIGS. 9 and 10. A circular sidewall 248 of the front seal 240 may include an annular ledge 250 that is configured to abut against an interior annular ledge 252 of the second cylindrical portion 228 of the housing. The outer diameter of the front seal 240 and the inner diameter of the second cylindrical portion 228 of the inner front portion 222 of the housing 220 are desirably about the same so that there is a nominal fit, or a slight interference fit, of the front seal 240 in the inner front portion 222 of the housing 220.

The first intermediate seal 242 and the second intermediate seal 244 may have substantially the same designs as the seals 68, 69 described above and illustrated in FIG. 4. For example, the first intermediate seal 242 may have a slit extending in a first direction and the second intermediate seal 244 may have a slit extending in a second direction that is oriented about 90° from the direction when the intermediate seals 242, 244 are disposed in an interior cavity formed by the cylindrical sidewall 248 of the front seal 240. As illustrated in FIGS. 13 and 14, the first intermediate seal 242 and the second intermediate seal 244 may each have at least one protrusion 254 and at least one recess 256 that is configured to receive the protrusion 254 of the other seal so that the first and second intermediate seals 242, 244 may interlock with each other in addition to interlocking with recesses 258 in an interior surface of the cylindrical sidewall 248.

The rear seal 246 includes a flange 260 that is configured to abut with a back end surface 262 (of the cylindrical sidewall 248) of the front seal 240, as illustrated in FIG. 12. The rear seal 246 also includes a web having an opening (not shown) that may be similar to the web 192 and the opening 190 of the rear seal 180 illustrated in FIG. 11. A front end surface 264 of the rear seal 246 is configured to abut the second intermediate seal 244. As illustrated in FIGS. 13 and 14, the inner back portion 224 of the housing 220 is in the form of a retaining ring that is configured to be press fit into the inner front portion 222 of the housing 220 such that a front end surface 266 of the inner back portion 224 of the housing 220 presses against the rear seal 260 so that the seals 240, 242, 244, 246 are in a compressed sandwich relation in an axial direction of the housing 220.

The elongated sheath 14, 114, 214 may be made out of any suitable material, including by not limited to polytetrafluoroethylene (PTFE), polyethylenebutylacrylate (PEBA), polyethylene, and polyimide.

The front seal 52, 160, 240, the first intermediate seal 68, 242, the second intermediate seal 69, 244, and the rear seal 76, 180, 246 may be made from the same material, which may be a silicone material having a Shore A durometer value in the range of about 35 to about 55, for example in the range of about 40 to about 50.

The outer housing 20, the inner housing 126, and the housing 220 may be made from a material that is stiffer or more rigid than the material used to make the front seal, the intermediate seals, and the rear seal so that the housings 20, 126, 220 act as an exoskeleton for the seals. In an embodiment, the housings 20, 126, 220 may be made from acrylonitrile butadiene styrene (ABS), or any other suitable plastic material that provides a relatively rigid structure as compared to the seals.

The outer housing 120 of the embodiment of FIGS. 5-7 may be made from a material that is stiffer than the material of the seals, but softer than the material of the inner housing 126. The outer housing 120 may be made from a silicone material having a Shore A durometer value in the range of about 60 to about 75, for example about 70.

The softness of the material used for the seals and tolerances provided by the openings and slits in the seals allow for a tighter fit between the seals and the implements and devices being inserted into the valve as compared to seals in the prior art, which allows the valve to provide for complete hemostasis for a wide range of diameters of implements and devices being inserted into the introducer sheath. Although such a tighter fit allows for complete hemostasis, the tighter fit may also generate higher frictional forces between the implements and devices being inserted into the introducer sheath and the seals within the introducer sheath.

Although conventional wisdom until now has been to reduce the perceived frictional forces, it has been unexpectedly found that the inner housing and the outer housing of embodiments according to the present invention allow the strain that is induced by the displacement of parts of the soft inner seal elements is allowed to fully recover and maintain hemostasis because of the seal element surrounding stiff outer housing. The strain recovery provided by the interaction between the inner and outer housings reduces the extent to which the operator of the introducer sheath feels an increased amount of frictional resistance that is generated between the seals and the implement or device. In other words, it has unexpectedly been found that embodiments according to the present invention provide an acceptable frictional resistance feel when using a wide range of diameters of implements and devices while still providing complete hemostasis across the entire range of diameters. In addition, it has been unexpectedly found that embodiments according to the present invention provide for complete hemostasis in conditions when the sheath has been inserted into a blood vessel and 1) nothing has been inserted into the valve (the relaxed closed slits of the intermediate seals block all potential penetrating blood flow), 2) a guide wire has been inserted into the valve (the hole (0.032 inches diameter) in the web 164 of the front seal is sized to seal on the guide wire (0.035 inches diameter) passing therethrough) (while the crossed slits 72 of the intermediate seals 68, 69 assure that the wire is held on the central axis of the seal set). The guide wire passing through the hole in the front seal, whose web has been reinforced by the housing 126 (acting as an exoskeleton) and thereby assuring the geometric integrity of the hole through the front seal and that the edges of the web 164 separated by the slit 170 is held and remains closed (preventing leakage therethrough), and 3) an 11 Fr (about 3.7 mm diameter) to 26 Fr (about 8.7 mm diameter) catheter has been inserted into the valve (the slit in the web of the front seal is elastically spread to an oval shape and would allow leakage therethrough, and because of the diameter of the hole in the rear seal, whose internal edges elastically contact and spread as the diameter of the catheter inserted therethrough increases in diameter, the rear seal creates a blood sealing contact with the perimeter of the catheter inserted therethrough. The ribs (on the distal side of the front seal) increase the section modulus of the front seal web 164 and establish a relationship with the elements proximal to the web 164 such that in a relaxed condition allow the web of the front seal and the intermediate seals 68, 69 to effectively resist the force exerted by blood pressure when no catheter or no guide wire is inserted (without the ribs 172, the force exerted by blood pressure would cause the web of the seal open at the slit 170), While at least one exemplary embodiment has been presented, it should be appreciated that a vast number of variations exist. It should also be appreciated that the exemplary embodiment or exemplary embodiments are only examples, and are not intended to limit the scope, applicability, or configuration of what may be understood thereby. Rather, the foregoing detailed description will provide those skilled in the art with a convenient roadmap for implementing an exemplary embodiments with, it being understood that various changes may be made in the function and arrangement of members described in an exemplary embodiment without departing from the scope of that described.

What is claimed is:

1. An introducer sheath comprising:
    an elongated sheath configured to be inserted into a blood vessel, the elongated sheath comprising a central lumen configured to allow a surgical implement or medical device to pass therethrough;
    a hemostatic valve operatively connected to the sheath, the hemostatic valve being configured to prevent blood in the blood vessel from exiting the introducer sheath assembly when the elongated sheath is located in the blood vessel, the hemostatic valve comprising
    a housing,
    a front seal disposed within and supported by the housing, the front seal comprising a cylindrical sidewall and a web extending transverse to the sidewall to define a cavity within the front seal, the web comprising a central opening without any device passing through the front seal, the central opening configured to provide a hemostatic seal with a guide wire when a portion of the guide wire is passed through the hemostatic valve, a first slit centered on the opening, and a plurality of elongated ribs equally spaced around the opening and radially extending away from the opening, the slit, the cavity, and the plurality of elongated ribs configured to allow the surgical implement or medical device to pass through the front seal;
    a first intermediate seal having a second slit oriented in a first direction, the first intermediate seal being supported by the front seal in the cavity;
    a second intermediate seal disposed in abutment with the first intermediate seal and being supported by the front seal in the cavity, the second intermediate seal having a third slit oriented in a second direction that is about 90° relative to the first direction,
    the first and second intermediate seals configured to support and center the guide wire in the central opening of the front seal when the portion of the guide wire is passed though the hemostatic valve, to allow the surgical implement or medical device to pass through the first intermediate seal and the second intermediate seal, and to create hemostasis when no guide wire, surgical implement, or medical device is present in the hemostatic valve, and
    a rear seal disposed in abutment with the front seal so that the first intermediate seal and the second intermediate seal are located in between the front seal and the rear seal, the rear seal having a web with an opening, the web configured to provide a hemostatic seal with a plurality of different sizes of surgical implements and medical devices when each implement and medical device is individually passed through the hemostatic valve, the plurality of different sizes ranging between about 3 mm and about 9 mm in diameter,
    the housing configured to provide strain recovery for strain induced displacement forces generated during movement of the implement or medical device through the front seal, the first intermediate seal, the second intermediate seal, and the rear seal.

2. The introducer sheath according to claim 1, wherein the front seal, the first intermediate seal, the second intermediate seal, and the rear seal each comprise a silicone having a Shore A durometer value of between about 35 and about 55.

3. The introducer sheath according to claim 2, wherein the silicone has a Shore A durometer value of between about 40 and about 50.

4. The introducer sheath according to claim 2, wherein the housing comprises a plastic material that is more rigid than the silicone.

5. The introducer sheath according to claim 1, wherein the central opening in the front seal has a diameter of between about 0.87 mm and about 0.90 mm.

6. The introducer sheath according to claim 5, wherein the diameter is about 0.89 mm.

7. The introducer sheath according to claim 1, wherein the plurality of ribs of the front seal are located within the cavity, and wherein the first intermediate seal abuts the plurality of ribs.

8. The introducer sheath according to claim 1, wherein the housing is configured to hold the front seal, the first intermediate seal, the second intermediate seal, and the rear seal in a compressed relation.

9. The introducer sheath according to claim 8, wherein the housing comprises a inner front portion and a inner back portion operatively connected to the inner front portion, the inner back portion configured to engage the rear seal and compress the rear seal against the front seal.

10. The introducer sheath according to claim 9, wherein the inner back portion of the housing comprises a retainer ring.

11. A hemostatic valve for an introducer sheath, the hemostatic valve comprising:
    a housing;
    a front seal disposed within and supported by the housing, the front seal comprising a cylindrical sidewall and a web extending transverse to the sidewall to define a cavity within the front seal, the web comprising a central opening without any device passing through the front seal, the central opening configured to provide a hemostatic seal with a guide wire when a portion of the guide wire is passed through the hemostatic valve, a first slit centered on the opening, and a plurality of elongated ribs equally spaced around the opening and radially extending away from the opening, the slit, and the plurality of elongated ribs configured to allow a surgical implement or medical device to pass through the front seal;
    a first intermediate seal having a second slit oriented in a first direction, the first intermediate seal being supported by the front seal in the cavity;
    a second intermediate seal disposed in abutment with the first intermediate seal and being supported by the front seal in the cavity, the second intermediate seal having a third slit oriented in a second direction that is about 90° relative to the first direction;
    the first and second intermediate seals configured to support and center the guide wire in the central opening of the front seal when the portion of the guide wire is passed though the hemostatic valve, and to allow the surgical implement or medical device to pass through the first intermediate seal and the second intermediate seal; and
    a rear seal disposed in abutment with the front seal so that the first intermediate seal and the second intermediate seal are located in between the front seal and the rear seal, the rear seal having a web with an opening, the web configured to provide a hemostatic seal with a plurality of different sizes of surgical implements and medical devices when each implement and medical device is individually passed through the hemostatic valve, the plurality of different sizes ranging between about 3 mm and about 9 mm in diameter,
    the housing configured to provide strain recovery for strain induced by displacement forces generated during movement of the implement or medical device through the front seal, the first intermediate seal, the second intermediate seal, and the rear seal.

12. The hemostatic valve according to claim 11, wherein the front seal, first intermediate seal, second intermediate seal, and rear seal each comprise a silicone having a Shore A durometer value of between about 35 and about 55.

13. The hemostatic valve according to claim 12, wherein the silicone has a Shore A durometer value of between about 40 and about 50.

14. The hemostatic valve according to claim 12, wherein the housing comprises a plastic material that is more rigid than the silicone.

15. The hemostatic valve according to claim 11, wherein the central opening in the front seal has a diameter of between about 0.87 mm and about 0.90 mm.

16. The hemostatic valve according to claim 15, wherein the diameter is about 0.89 mm.

17. The hemostatic valve according to claim 11, wherein the plurality of ribs of the front seal are located within the cavity, and wherein the first intermediate seal abuts the plurality of ribs.

18. The hemostatic valve according to claim 11, wherein the housing is configured to hold the front seal, the first intermediate seal, the second intermediate seal, and the rear seal in a compressed relation.

19. The hemostatic valve according to claim 11, wherein the housing comprises an inner front portion and a inner back portion operatively connected to the inner front portion, the inner back portion configured to engage the rear seal and compress the rear seal against the front seal.

20. The hemostatic valve according to claim 19, wherein the inner back portion of the housing comprises a retainer ring.

* * * * *